(12) United States Patent
Barth et al.

(10) Patent No.: US 7,114,378 B1
(45) Date of Patent: Oct. 3, 2006

(54) PLANAR RESONANT TUNNELING SENSOR AND METHOD OF FABRICATING AND USING THE SAME

(75) Inventors: Philip W. Barth, Loveland, CO (US); Derek Stein, Loveland, CO (US); Curt Flory, Loveland, CO (US); Rick Pittaro, Loveland, CO (US); Daniel Roitman, Loveland, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/107,996

(22) Filed: Apr. 14, 2005

(51) Int. Cl.
*G01B 5/28* (2006.01)
(52) U.S. Cl. ....................................... 73/105
(58) Field of Classification Search ............... None
See application file for complete search history.

(56) References Cited

U.S. PATENT DOCUMENTS

| | | | |
|---|---|---|---|
| 5,795,782 A | 8/1998 | Church et al. | |
| 5,932,876 A * | 8/1999 | Niedermann | 250/306 |
| 5,982,608 A * | 11/1999 | Kalnitsky et al. | 361/288 |
| 6,015,714 A | 1/2000 | Baldarelli et al. | |
| 6,267,872 B1 | 7/2001 | Akeson et al. | |
| 6,362,002 B1 | 3/2002 | Denison et al. | |
| 6,464,842 B1 | 10/2002 | Golovchenko et al. | |
| 6,474,133 B1 * | 11/2002 | Okada | 73/1.38 |
| 6,627,067 B1 | 9/2003 | Branton et al. | |
| 6,673,615 B1 | 1/2004 | Denison et al. | |
| 6,674,594 B1 | 1/2004 | Wakabayashi et al. | |
| 6,706,203 B1 | 3/2004 | Barth et al. | |
| 6,706,204 B1 | 3/2004 | Roitman et al. | |
| 6,783,643 B1 | 8/2004 | Golovchenko et al. | |
| 6,843,281 B1 | 1/2005 | Barth et al. | |
| 6,846,702 B1 | 1/2005 | Barth | |
| 2002/0130333 A1 * | 9/2002 | Watanabe et al. | 257/200 |
| 2002/0132500 A1 * | 9/2002 | Watanabe et al. | 439/43 |
| 2003/0044816 A1 | 3/2003 | Denison et al. | |
| 2003/0066749 A1 | 4/2003 | Golovchenko et al. | |
| 2003/0080042 A1 | 5/2003 | Barth et al. | |
| 2003/0104428 A1 | 6/2003 | Branton et al. | |
| 2004/0132070 A1 * | 7/2004 | Star et al. | 435/6 |
| 2005/0014162 A1 | 1/2005 | Barth et al. | |
| 2005/0017173 A1 * | 1/2005 | Kumar | 250/306 |
| 2005/0022895 A1 | 2/2005 | Barth et al. | |
| 2005/0069687 A1 | 3/2005 | Barth | |
| 2005/0070042 A1 | 3/2005 | Barth | |

FOREIGN PATENT DOCUMENTS

WO       WO 00/34527       6/2000

OTHER PUBLICATIONS

Bakkers et al. "Shell-Tunneling Spectroscopy of the Single-Particle Energy Levels of Insulating Quantum Dots," (2001) Nano Letters, vol. 1(10):551-556.

(Continued)

*Primary Examiner*—Robert Raevis

(57) ABSTRACT

Planar resonant tunneling sensor devices and methods for using the same are provided. The subject devices include first and second electrodes present on a surface of a planar substrate and separated from each other by a nanodimensioned gap. The devices also include a first member for holding a sample, and a second member for moving the first member and planar resonant tunneling electrode relative to each other. Also provided are methods of fabricating such a device and methods of using such a device for improved detection and characterization of a sample.

18 Claims, 13 Drawing Sheets

OTHER PUBLICATIONS

Chang et al. "Resonant Tunneling in Semiconductor Double Barriers," (1974) Applied Physics Letters, 24(12):593-595.

Goodhue et al. "Large Room-Temperature Effects from Resonant Tunneling Through AlAs Barriers," (1986) Appl. Phys. Lett. 49(17):1086-1088.

Sollner et al. "Resonant Tunneling Through Quantum Wells at Frequencies Up to 2.5THz," (1983) Appl. Phys. Lett. 43(6):588-590.

Esaki et al. "Superlattice and Negative Differential Conductivity In Semiductors," (1970) IBM J. Res Development, 14:61-65.

Sollner et al. "Quantum Well Oscillators," (1984) Appl. Phys. Lett. 45(12):1319-1321.

* cited by examiner

PLANAR RESONANT TUNNELING SENSOR AND METHOD OF FABRICATING AND USING THE SAME

BACKGROUND OF THE INVENTION

The quantum mechanical phenomenon of "resonant tunneling" was first analyzed in 1969 by Esaki and Tsu in 1969 (Esaki et al., *IBM J. Res. and Develop.* 14:61–69 (1970). The concept of "resonant tunneling" has since evolved into that of the "resonant tunneling diode" (RTD), wherein a central region containing some central moiety, for example a quantum dot, is placed between two quantum mechanical tunneling barriers. Two conducting electrodes in contact with the two quantum mechanical tunneling barriers can therefore allow the injection of electrical current from a first electrode, across a first barrier to the moiety, and from the moiety across a second barrier to the second electrode.

If an energy level in the central moiety matches the electron energy in the first electrode, some enhancement of electrical current through the RTD occurs. This phenomenon can be called matched-level resonance.

If the matched-level resonance condition is present, and if in addition the two quantum mechanical tunneling barriers are equal in magnitude, a tremendous additional enhancement in electrical current through the RTD occurs. This second phenomenon wherein the two quantum mechanical tunneling barriers are equal in magnitude can be called matched-barrier resonance.

A variant of the resonant tunneling diode is used with a scanning tunneling microscope (STM) in a procedure called "resonant tunneling spectroscopy," which has been refined into a procedure called "shell tunneling spectroscopy" (Bakkers, et al., *Nano Letters*, 1(10):551–556 (2001)).

The prior shell-tunneling spectroscopy work has been limited because the sample under test is fixed in place in a single position on top of an insulator of constant thickness. In order for the desirable phenomenon matched-barrier resonance to be employed in such a device, the magnitude of the upper quantum mechanical tunneling barrier due to the separation of the STM tip from the sample under test must be matched to the magnitude of the lower quantum mechanical tunneling barrier due to the presence of the insulator between the sample under test and the conducting substrate, and this is difficult to achieve in practice.

Thus there exists a need for a tunneling spectrometer in which the phenomenon of matched-barrier resonance can be effectively employed, and at the same time the phenomenon of matched-energy resonance can also be made to occur, in order to obtain a complete density of states for a test sample. The present invention addresses this need.

Relevant Literature

Bakkers et al., *Nano Letters*, 1(10):551–556 (2002); Chang et al., *Applied Physics Lett.*, 24(12):593–595 (1974); Goodhue et al., *Applied Physics Lett.*, 49(17):1086–1088 (1986); Sollner et al., *Applied Physics Lett.*, 43(6):588–590 (1983); Esaki et al., *IBM J. Res. Dev.*, 14:61–65 (1970); and Sollner et al., *Applied Physics Lett.*, 45(12):1319–1321 (1984).

SUMMARY OF THE INVENTION

Planar resonant tunneling sensors and methods for using the same are provided. The subject sensors include first and second electrodes present on a surface of a planar substrate and separated from each other by a nanodimensioned gap. The devices further include a first member for holding a sample, and a second member for moving said first member and planar resonant tunneling electrode relative to each other. Also provided are methods of fabricating such a device and methods of using such a device for improved detection and characterization of a sample.

One feature of the invention provides a device including a planar resonant tunneling sensor including first and second electrodes present on a surface of a planar substrate and separated from each other by a nanodimensioned gap, a first member for holding a sample, and a second member for moving said first member and planar resonant tunneling electrode relative to each other. In some embodiments, the first and second members comprise an integrated structure. In further embodiments, the integrated structure is an atomic force microscopy (AFM) tip. In other embodiments, the nanodimensioned gap has a width ranging in length from about 1 to about 8 nm. In some embodiments, the second member moves the first member sequentially across the first electrode, nanodimensioned gap and second electrode at a distance ranging from about 0.1 nm to about 10 nm.

In some embodiments, the nanodimensioned gap includes an insulating material. In such embodiments, the insulating material may be silicon dioxide. In some embodiments, the first and second electrodes comprise platinum or polycrystalline silicon. In further embodiments, the planar substrate includes single-crystal silicon.

Another feature of the invention provides a method for fabricating a planar resonant tunneling sensor, the method including providing a first insulating layer atop a planar substrate, depositing a first conductive layer on a first portion of a surface of the first insulating layer, depositing a spacer layer over the first conductive layer and a second portion of the surface of the first insulating layer, depositing a second conductive layer over a portion of the surface of the second insulating layer, and removing a portion of the deposited second conductive layer and the insulator layer to produce a planar resonant tunneling electrode sensor comprising first and second electrodes present on a surface of a planar substrate and separated from each other by a nanodimensioned gap. A portion of the spacer layer in the nanodimensioned gap, and extending from the upper extent of the nanodimensioned gap downward to the first insulating layer, may subsequently be removed, for example by chemical etching. If the spacer layer comprises an insulating material it may be left in place.

A further feature of the invention provides a method of forming a nanodimensioned gap suitable for various purposes, for example to serve as electrical contacts to nanoscale devices comprising diodes, transistors, and the like.

In some embodiments the removal of a portion of the deposited second conductive layer includes polishing the surface to produce a flat surface. In further embodiments, the polishing includes using a chemomechanical polishing protocol. In some embodiments, the method further includes positioning the sensor in a device that further includes a first member for holding a sample and a second member for moving the first member and planar resonant tunneling sensor relative to each other.

Yet another feature of the present invention provides a method including positioning a sample on a first member of a device including a planar resonant tunneling sensor comprising first and second electrodes present on a surface of a planar substrate and separated from each other by a nanodimensioned gap, a first member for holding a sample, and a second member for moving said first member and planar resonant tunneling electrode relative to each other, and moving the positioned sample relative to the planar resonant tunneling sensor while monitoring the current between the first and second electrodes.

In some embodiments, the method includes maintaining a constant first voltage applied to the sensor while the sample is moved relative to said sensor. In some embodiments the method further includes reiterating moving the positioned sample relative to the planar resonant tunneling sensor while monitoring the voltage between the first and second electrodes at least once at a second voltage that is different from the first voltage. In some embodiments, the method is a method for characterizing a quantum dot, a macromolecule, or a nanocrystal.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
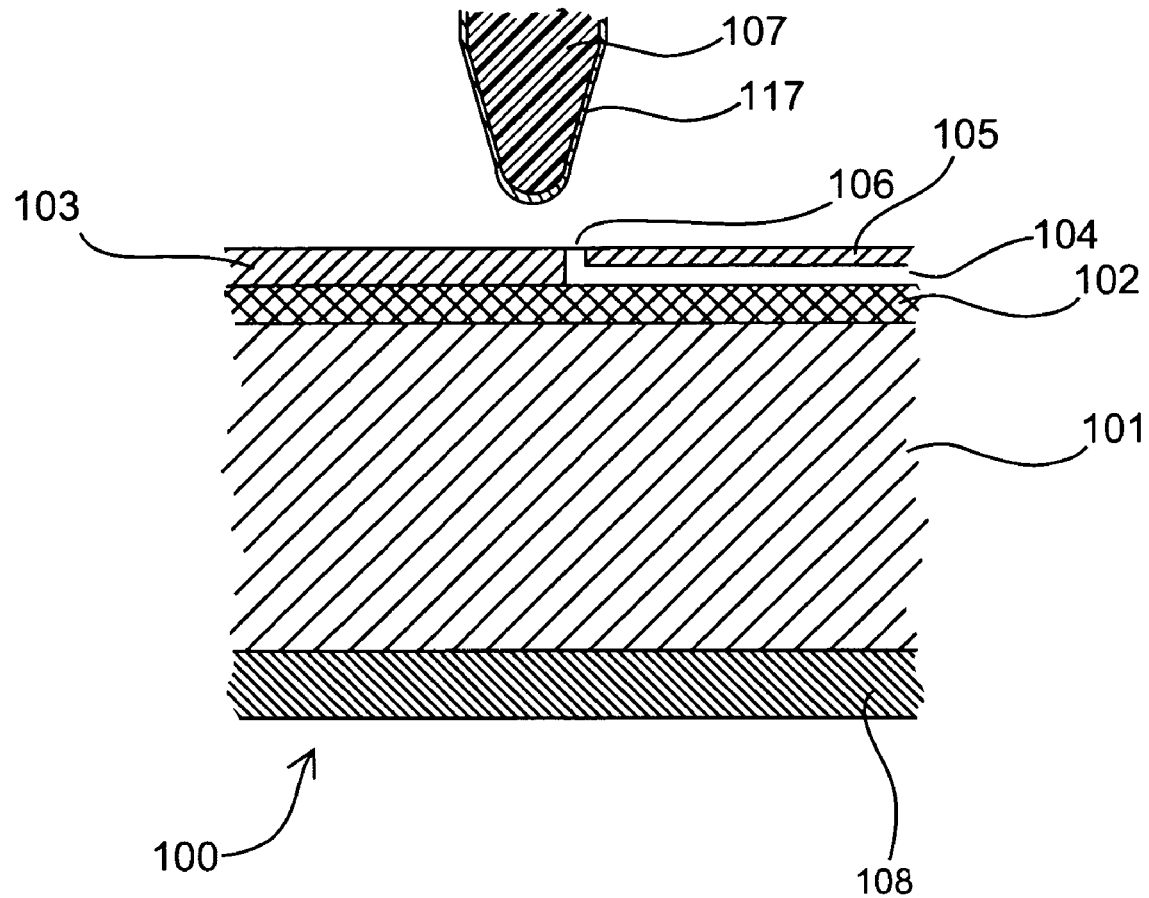
FIG. 1 is a schematic illustration of a cross-section at plane 1a of FIG. 3 of an embodiment 100 of the present invention.

A "biopolymer" is a polymer of one or more types of repeating units, regardless of the source (e.g., biological (e.g., naturally-occurring, obtained from a cell-based recombinant expression system, and the like) or synthetic). Biopolymers may be found in biological systems and particularly include polypeptides, polynucleotides, proteoglycans, etc., including compounds containing amino acids, nucleotides, or a mixture thereof.

The terms "polypeptide" and "protein" are used interchangeably throughout the application and mean at least two covalently attached amino acids, which includes proteins, polypeptides, oligopeptides and peptides. A polypeptide may be made up of naturally occurring amino acids and peptide bonds, synthetic peptidomimetic structures, or a mixture thereof. Thus "amino acid", or "peptide residue", as used herein encompasses both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the D- or the L-configuration.

In general, biopolymers, e.g., polypeptides or polynucleotides, may be of any length, e.g., greater than 2 monomers, greater than 4 monomers, greater than about 10 monomers, greater than about 20 monomers, greater than about 50 monomers, greater than about 100 monomers, greater than about 300 monomers, usually up to about 500, 1000 or 10,000 or more monomers in length. "Peptides" and "oligonucleotides" are generally greater than 2 monomers, greater than 4 monomers, greater than about 10 monomers, greater than about 20 monomers, usually up to about 10, 20, 30, 40, 50 or 100 monomers in length. In certain embodiments, peptides and oligonucleotides are between 5 and 30 amino acids in length.

The terms "polypeptide" and "protein" are used interchangeably herein. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids. The term "fusion protein" or grammatical equivalents thereof references a protein composed of a plurality of polypeptide components, that while typically not attached in their native state, typically are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, and the like.

A "monomeric residue" of a biopolymer is a subunit, i.e., monomeric unit, of a biopolymer. Nucleotides are monomeric residues of polynucleotides and amino acids are monomeric residues of polypeptides.

A "substrate" refers to any surface that may or may not be solid and which is capable of holding, embedding, attaching or which may comprise the whole or portions of an excitable molecule.

The term "nanodimensional" or "nanodimensioned" refers to a feature ranging in size from about 0.5 nm to around 300 nm in diameter.

The term "tunneling" refers to quantum mechanical tunneling, comprising the movement of a particle from one location to another through an energy barrier which would, in the absence of quantum mechanical effects, prevent the movement of the particle through the energy barrier.

The term "resonant tunneling" refers to the tunneling of a particle, typically an electron, from one location to another through two or more energy barriers enclosing one or more quantum well states situated between the locations. The one location and another typically comprise electrodes.

Resonant tunneling comprises two effects, one called "matched level resonance" and one called "matched barrier resonance."

Matched level resonance may be detected as enhanced conduction between two electrodes as seen in a plot of the differential of current with respect to voltage when plotted versus applied voltage, i.e., a peak in dI/dV versus V, where I is current, V is applied voltage, and dI/dV is the differential of current with respect to voltage.

Matched barrier resonance may be detected, when the condition of matched level resonance is also present, as greatly enhanced conduction between two electrodes as seen in a plot of current with respect to voltage when plotted versus applied voltage, i.e., a peak in I versus V.

The term "ramping potential" or "bias potential" refers to having the ability to establish a variety of different voltages over time. In certain cases, this may be referred to as a "scanning voltage," "ramping voltage," or time varying voltage. A ramping potential may provided by a "ramping potential-providing element" or a "potential-providing element".

"Hybridizing", "annealing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" is a particular sub-class of binding efficiency, and refers to binding efficiency in the case where the binding components are polynucleotides.

It will also be appreciated that throughout the present application, that words such as "first", "second" are used in a relative sense only. A "set" may have one type of member or multiple different types. "Fluid" is used herein to reference a liquid.

The terms "symmetric" and "symmetrized" refer to the situation in which the tunneling barriers from each electrode to the biopolymer are substantially equal in magnitude.

The terms "portion" and "portion of a biopolymer" refer to a part, subunit, monomeric unit, portion of a monomeric unit, atom, cluster of atoms, charge or charged unit.

In many embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

The term "adjacent" refers to anything that is near, next to or adjoining. For instance, a nanopore referred to as "adjacent to an excitable molecule" may be near an excitable molecule, it may be next to the excitable molecule, it may pass through an excitable molecule or it may be adjoining the excitable molecule. "Adjacent" can refer to spacing in linear, two-dimensional and three-dimensional space. In general, if a quenchable excitable molecule is adjacent to a nanopore, it is sufficiently close to the edge of the opening of the nanopore to be quenched by a biopolymer passing through the nanopore. Similarly, electrodes that are positions adjacent to a nanopore are positioned such that resonance tunneling occurs a biopolymer passes through the nanopore. Compositions that are adjacent may or may not be in direct contact.

If one composition is "bound" to another composition, the bond between the compositions does not have to be in direct contact with each other. In other words, bonding may be direct or indirect, and, as such, if two compositions (e.g., a substrate and a nanostructure layer) are bound to each other, there may be at least one other composition (e.g., another layer) between to those compositions. Binding between any two compositions described herein may be covalent or non-covalent.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present, and/or determining whether it is present or absent.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

DETAILED DESCRIPTION OF THE INVENTION

Planar resonant tunneling sensors and methods for using the same are provided. The subject sensors include first and second electrodes present on a surface of a planar substrate and separated from each other by a nanodimensioned gap, a first member for holding a sample, and a second member for moving said first member and planar substrate relative to each other. Also provided are methods of fabricating such a device and method of using such a device for improved detection and characterization of a nanoscale moiety such a biopolymer.

Before the present invention described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a biopolymer" includes a plurality of such biopolymers and reference to "the electrode" includes reference to one or more electrodes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The Subject Devices

Figure 2A:
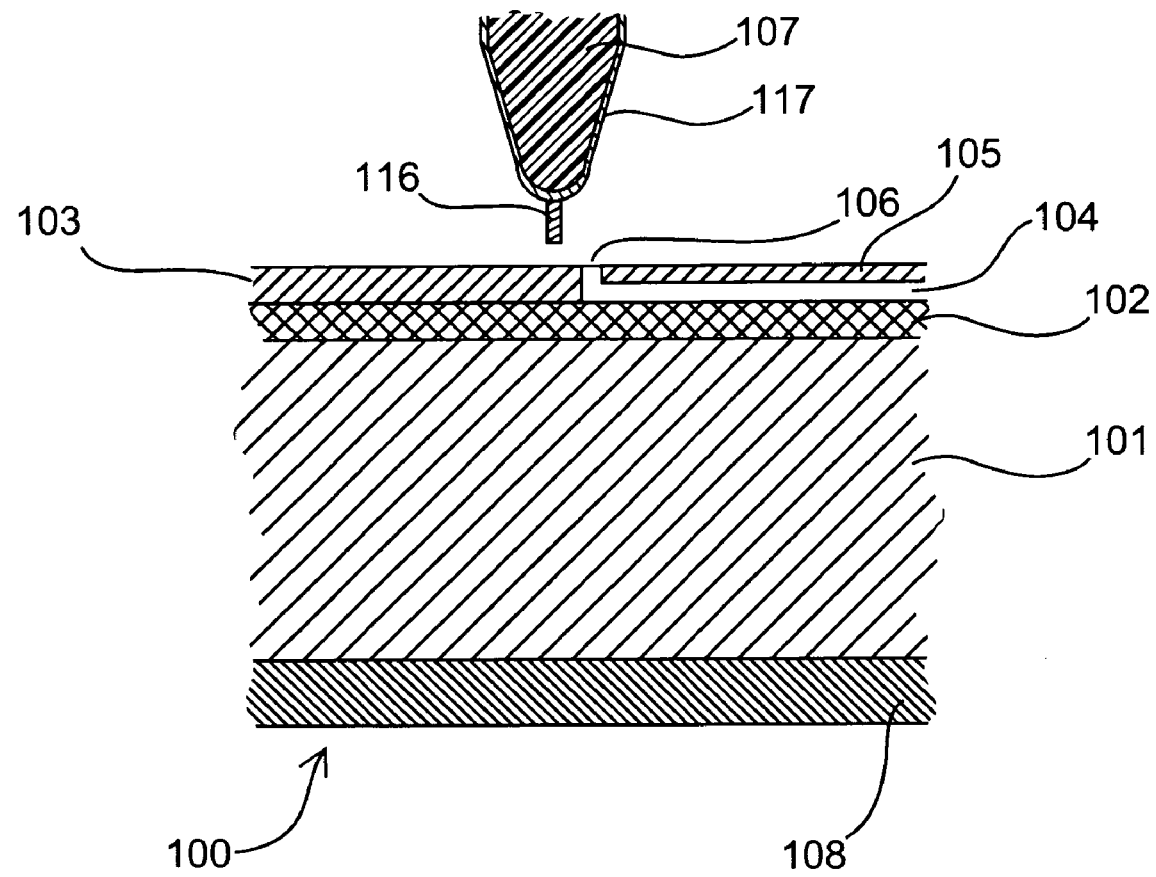
FIGS. 2A and 2B are schematic illustrations of cross-sections at plane 1a of FIG. 3 of an embodiment 100 of the present invention with additional elements and a sample 116 present in the first member for holding a sample 107. The arrow shows the direction the sample is moved over the nanodimensioned gap
Figure 2B:
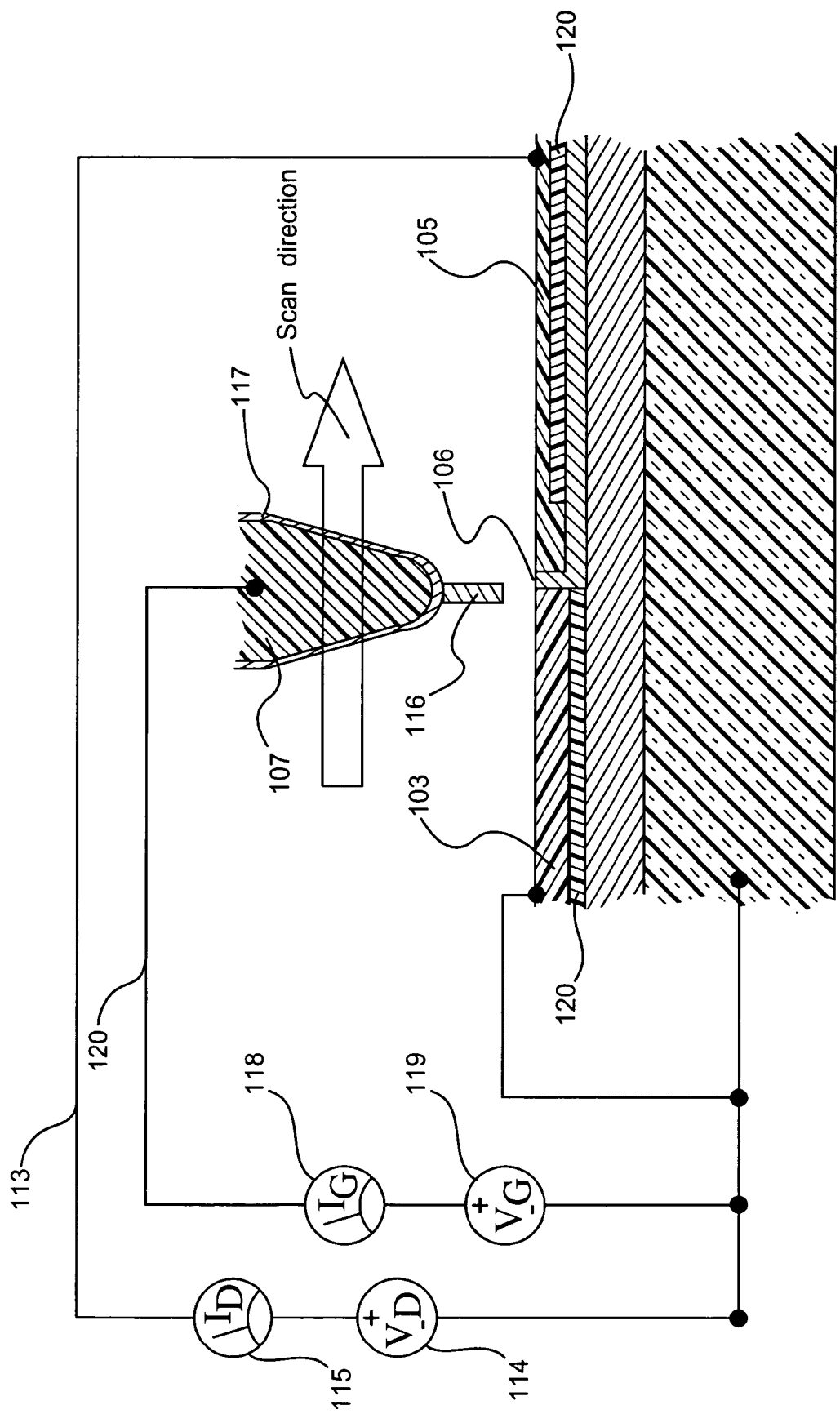
Figure 3:
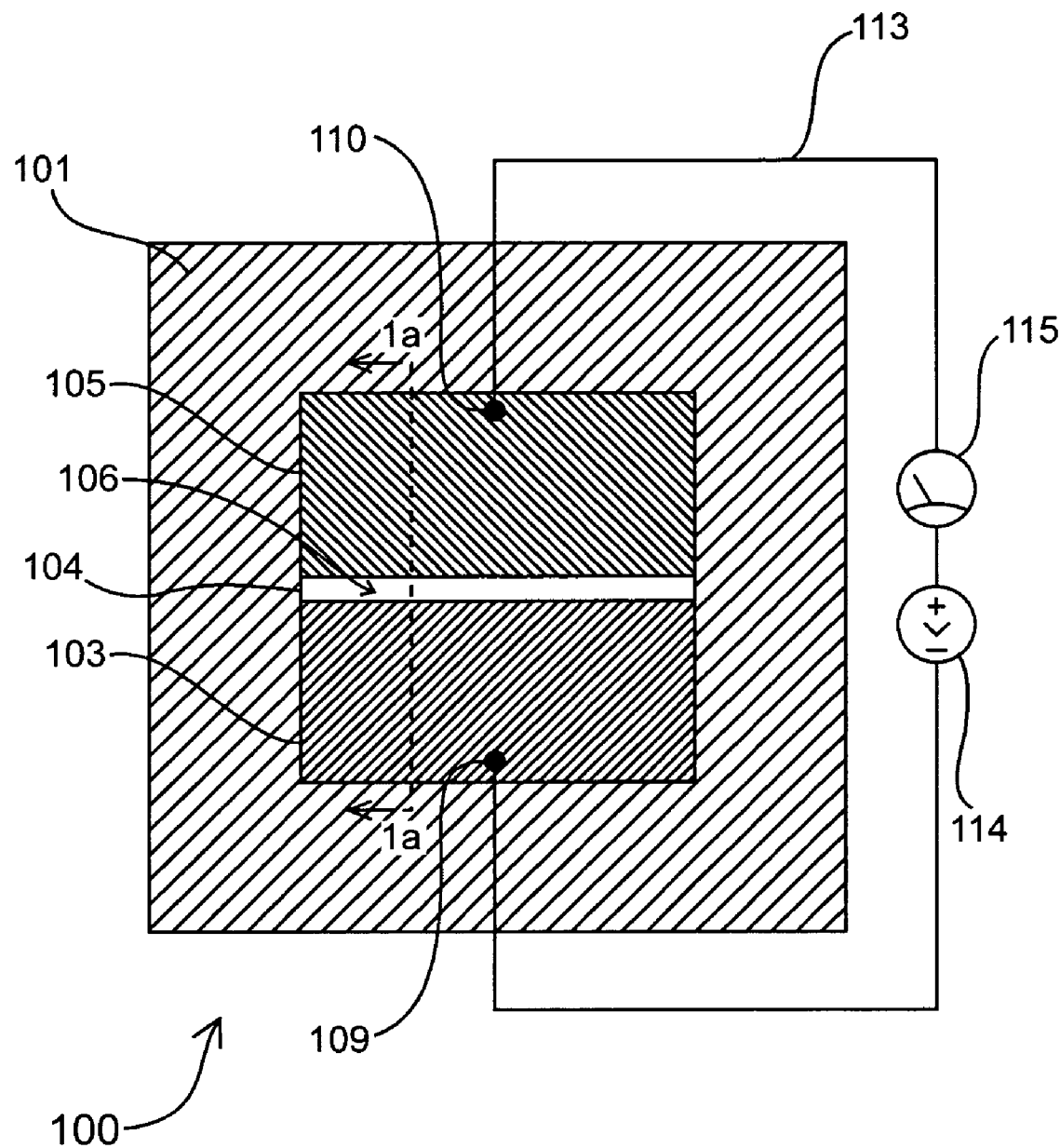
FIG. 3 is a schematic illustration of a top plan view of an embodiment 100 of the present invention.

The present invention provides devices including a planar resonant tunneling sensor. FIGS. 1 and 2A–2B illustrate cross-sections and FIG. 3 illustrated a top plan view of an embodiment 100 of the present invention, and are used in the flowing description. In general, the device of the present invention includes a planar resonant tunneling sensor present on the surface of a planar substrate 101 and a first member 107 for holding a sample and a second member 108 for moving the first member 107 and the planar resonant tunneling sensor relative to each other. The planar resonant tunneling sensor includes a first 103 and second 105 electrode elements separated by a nanodimensioned gap 106.

The planar substrate 101 may comprise of a variety of materials known in the art for designing substrates and nanopores. A substrate suitable for use with the subject device may include one or more layers of one or more materials including, but not limited to, single-crystal silicon, silicon nitride, silicon dioxide, platinum or other metals, silicon oxynitride, silicon rich nitride, organic polymers, and other insulating layers, carbon based materials, plastics, metals, or other materials known in the art for etching or fabricating semiconductor or electrically conducting materials. A suitable substrate need not be of uniform thickness. The substrate may or may not be a solid material, and for example may comprise in part or in whole a mesh, wire, or other material on which a planar resonant tunneling sensor may be constructed. The substrate may comprise various shapes and sizes. However, it must be large enough and of sufficient width to be capable of supporting a planar resonant tunneling sensor. In representative embodiments, the substrate has a width ranging from about 1 mm to about 10 mm, such as from about 3 mm to about 5 mm. In representative embodiments, the substrate has a thickness ranging from about 50 μm to about 2.5 mm, such as from about 200 μm to about 600 μm. In addition, the substrate may comprise of various structural properties, such as rigid or flexible. However, the substrate must be sufficiently rigid enough to support the elements of the planar resonant tunneling sensor.

In addition, the device 100 of the present invention includes a planar resonant tunneling sensor. The term "resonant tunneling" refers to the tunneling of a particle, typically an electron, from one location to another through two or more energy barriers enclosing one or more quantum well states situated between the locations. The one location and another typically comprise electrodes.

Resonant tunneling comprises two effects, one called "matched level resonance" and one called "matched barrier resonance."

Matched level resonance may be detected as enhanced conduction between two electrodes as seen in a plot of the differential of current with respect to voltage when plotted versus applied voltage, i.e., a peak in dI/dV versus V, where I is current, V is applied voltage, and dI/dV is the differential of current with respect to voltage.

Matched barrier resonance may be detected, when the condition of matched level resonance is also present, as greatly enhanced conduction between two electrodes as seen in a plot of current with respect to voltage when plotted versus applied voltage, i.e., a peak in I versus V.

A suitable planar resonant tunneling sensor for use with subject invention includes a first 103 and second 105 electrodes separated by a nanodimensioned gap 106. In some embodiments, the nanodimensioned gap 106 includes a spacer element 104. In some embodiments the spacer element 104 may comprise an insulator.

In some embodiments, the first 103 and second 105 electrodes will have a thickness ranging from about 0.1 µm to about 5 µm, including from about 0.5 µm to about 1 µm. In certain embodiments, the spacer element 104 will have a thickness ranging from about 0.5 nm to about 10 nm, including from about 1 nm to about 9 nm, from about 2 nm to about 7 nm, from about 3 nm to about 6 nm, including about 4 nm to about 5 nm. In certain embodiments, the nanodimensioned gap 106 will have a width ranging from about ranging from about 0.5 nm to about 10 nm, including from about 1 nm to about 9 nm, from about 2 nm to about 7 nm, from about 3 nm to about 6 nm, including about 4 nm to about 5 nm.

The first 103 and second 105 electrodes may be made up of a variety of electrically conductive materials. Such materials include, but are not limited to, metals, silicides, polycrystalline silicon, organic conductors and superconductors, electrically conductive metals and alloys of tin, copper, zinc, iron, magnesium, cobalt, nickel, platinum, and vanadium. Other materials well known in the art that provide for electrical conduction may also be employed. The spacer element 104 may be made up of a variety of materials that provide for insulation between the first 103 and second 105 electrodes. A variety of suitable materials are well known in the art and may be used with the subject device. Representative materials include, for example, silicon dioxide, silicon nitride, silicon oxynitride, silicon rich nitride, organic polymers, and plastics, etc. The spacer element 104 may also be made up of a variety of electrically conductive materials. Such materials include, but are not limited to, metals, silicides, polycrystalline silicon, organic conductors and superconductors, electrically conductive metals and alloys of tin, copper, zinc, iron, magnesium, cobalt, nickel, platinum, and vanadium. The spacer element 104 may be removed, for example by means comprising chemical etching, in the region of nanodimensioned gap 106 and extending downward to first insulating layer 102.

Referring to FIGS. 1 and 2A, the subject device 100 further includes a first member 107 for holding a sample above the planar resonant tunneling sensor and a second member 108 for moving the first member 107 and the planar resonant tunneling sensor relative to each other. The first member 107 can be made of a variety of materials that are capable of holding a sample in position above the planar resonant tunneling sensor. In some embodiments the first member 107 is non-conductive and is an atomic force microscope (AFM) tip. In other embodiments the first member 107 is conductive and is a scanning tunneling microscope (STM) tip. In representative embodiments, the first element 107 holds the sample above first electrode 103, nanodimensioned gap 106 and second electrode 105 at a distance from about 0.1 nm to about 100 nm, including from about 0.5 nm to about 10 nm, such as from about 1 nm to about 2 nm. The second member 108 can be made of a variety of materials to provide an element that is capable of moving the first member 107 and the planar resonant tunneling sensor relative to each other. In some embodiments, the first member 107 and the second member 108 are separate units that do not comprise a single integrated structure. In certain embodiments, the first member 107 and second member 108 are a single integrated structure. In some embodiments the first member 107 and the second member 108 are an integrated structure in which the first member 107 is an AFM tip and the second member is the movement mechanisms of an AFM device associated with the tip, as found in AFM devices. In other embodiments the first member 107 and the second member 108 are an integrated structure in which the first member 107 is an STM tip and the second member is the movement mechanisms of an STM device associated with the tip, as found in STM devices. In further embodiments, the first member 107 may further include an optional insulating material 117.

Referring to FIG. 3, the subject device 100, in some embodiments, will further include an element 114 for applying an electrical voltage between the first 103 and second 105 electrodes. The electrical voltage generating element 114 may be positioned anywhere relative to the substrate 101, the nanodimensional gap 106, the first electrode 103 and the second electrode 105. The electrical voltage generating element 114 should be capable of ramping to establish a time-varying voltage between the first electrode 103 and the second electrode 105. A variety of electrical voltage generating elements 114 may be employed with the present invention. A number of these electrical voltage generating elements 114 are known in the art. The electrical voltage generating element 114 has the ability to ramp to establish the time-varying voltage between the first electrode 103 and the second electrode 105.

In certain embodiments, the subject device 100, will further include an element 115 for measuring an electrical current between the first 103 and second 105 electrodes. The electrical current measuring element 115, may be any structure, component or apparatus that is well known in the art and that may be electrically connected 113 to one or more components of the present invention. The device may further include other elements of the output generating system, including data acquisition software, an electronic storage medium, etc.

Referring to FIG. 2B, the subject device 100, in some embodiments, will further include an element 119 for applying an electrical voltage between the first 103 electrode and first member for holding a sample 107. The electrical voltage generating element 119 may be positioned anywhere relative to the substrate 101, the nanodimensional gap 106, the first electrode 103 and the first member for holding a sample 107. The electrical voltage generating element 114 should be capable of ramping to establish a time-varying voltage between the first electrode 103 and the first member for holding a sample 107. A variety of electrical voltage generating elements 119 may be employed with the present invention. A number of these electrical voltage generating elements 119 are known in the art. The electrical voltage generating element 119 has the ability to ramp to establish the time-varying voltage between the first electrode 103 and the first member for holding a sample 107.

In certain embodiments, the subject device 100, will further include an element 118 for measuring an electrical current between the first 103 electrode and the first member for holding a sample 107. The electrical current measuring element 118, may be any structure, component or apparatus that is well known in the art and that may be electrically connected 120 to one or more components of the present invention. The device may further include other elements of the output generating system, including data acquisition software, an electronic storage medium, etc.

Fabrication of the Subject Devices

Having described representative embodiments of the device of the invention, a description of representative embodiments of methods of fabrication of the invention is now provided. A non-limiting exemplary method of fabricating an embodiment of the subject device 100 is provided in FIGS. 4A–4F, 5A–5B, and 6A–6B. The figures are not necessarily drawn to scale. For example, the width of the nanodimensioned gap is exaggerated in order to make it visible at the drawing scale. In general fabrication of the subject device 100 includes first fabricating a planar resonant tunneling sensor and then positioning the planar resonant tunneling sensor in a device that further includes a first member 107 for holding a sample and a second 108 member for moving the first member 107 and the planar resonant tunneling sensor relative to each other.

Figure 4A:
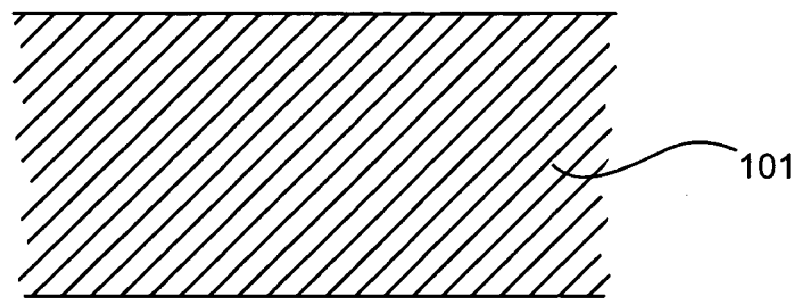
FIGS. 4A–4F illustrate sequential steps of a method of fabricating embodiment 100 of the present invention.
Figure 4B:
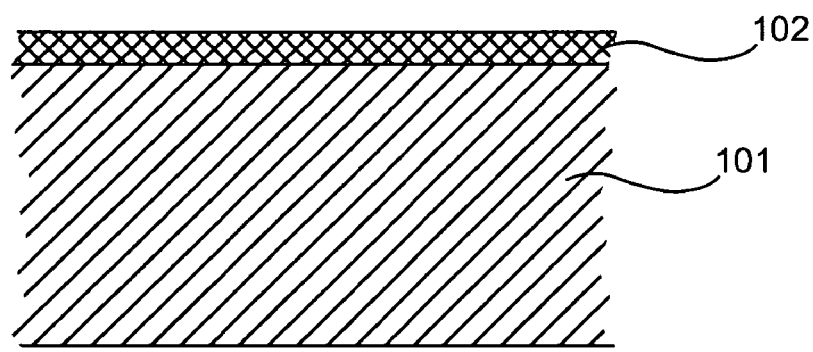

In an exemplary embodiment, fabrication of the planar resonant tunneling sensor begins, as exemplified in FIGS. 4A and 4B with providing a substrate 101 and forming a first insulating layer 102 atop substrate 101. The first insulating layer 102 may be formed atop the substrate 101 by a variety of deposition method known in art, such as, for example, TEOS oxide deposition. The insulating layer 102, may include one or more of one of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, and plasma nitride. In some embodiments, the insulating layer 102 comprises silicon dioxide.

The first insulating layer 102 may be formed atop substrate 101 by a variety of deposition methods known in the art. For example, a deposition source, such as a vacuum evaporation source or a molecular beam epitaxy source or a sputtering source is used to deposit the first insulating layer 102 atop substrate 101. Next, a lithography step is performed, and etching is performed in a dilute solution of aqua regia, comprising a mixture of hydrochloric acid and nitric acid, to define the lateral extent of the first insulating layer 102. Alternatively, a photolithography step may be performed prior to the deposition step and first insulating layer 102 may be defined by means of a lift-off process.

The insulating layer 102 may comprise various shapes and sizes. However, it must be large enough and of sufficient width to be capable of supporting a planar resonant tunneling sensor. In representative embodiments, the insulating layer 102 covers the entire upper surface of substrate 101. In representative embodiments, the insulating layer 102 has a thickness ranging from about 0.1 µm to about 5 µm, including from about 0.5 µm to about 4 µm, such as from about 2 µm to about 3 µm. In representative embodiments, the insulating layer 102 has a thickness of about 1 µm.

Figure 4C:
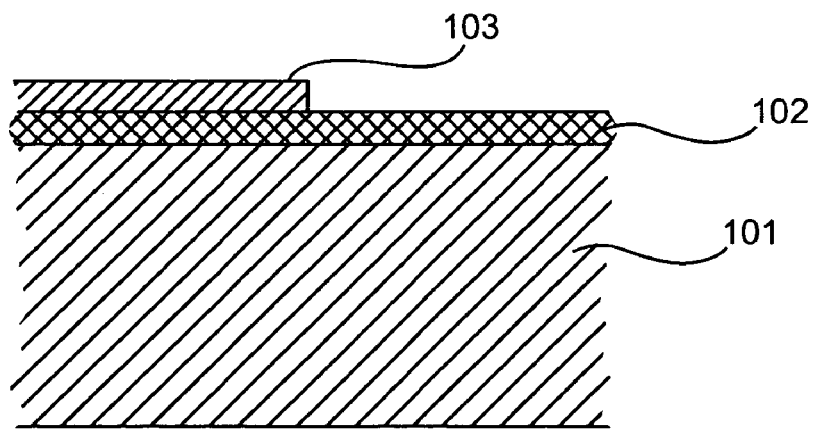

The exemplary fabrication method of the planar resonant tunneling sensor continues as shown in FIG. 4C by forming the first electrode 103 atop a first portion of the insulating layer 102. The first electrode 103 may be made up of a variety of electrically conductive materials. Such materials include, but are not limited to, metals, silicides, such as polycrystalline silicon, organic conductors and superconductors, electrically conductive metals and alloys of tin, copper, zinc, iron, magnesium, cobalt, nickel, platinum, and vanadium. Other materials well known in the art that provide for electrical conduction may also be employed. In certain embodiments, the first electrode 103 is made of polycrystalline silicon. In other embodiments, the first electrode 103 is made of platinum.

The first electrode 103 may be formed atop a first portion of the insulating layer 102 by a variety of deposition methods known in the art. For example, a deposition source, such as a vacuum evaporation source or a molecular beam epitaxy source or a sputtering source is used to deposit the first electrode 103 atop a first portion of the insulating layer 102. Next, a lithography step is performed, and etching is performed in a dilute solution of aqua regia, comprising a mixture of hydrochloric acid and nitric acid, to define the lateral extent of the first electrode 103. Alternatively, a photolithography step may be performed prior to the deposition step and first electrode 103 may be defined by means of a lift-off process.

The first electrode 103 may comprise various shapes and sizes. However, it must be large enough and of sufficient width to be capable of forming a planar resonant tunneling sensor. In representative embodiments, the first electrode 103 has a width ranging from about 0.5 µm to about 25 µm, such as from about 1 µm to about 5 µm. In representative embodiments, the first electrode 103 has a thickness ranging from about 0.1 µm to about 5 µm, including from about 0.5 µm to about 3 µm, such as from about 0.75 µm to about 2 µm. In certain embodiments, the first electrode 103 has a thickness of about 1 µm.

Figure 4D:
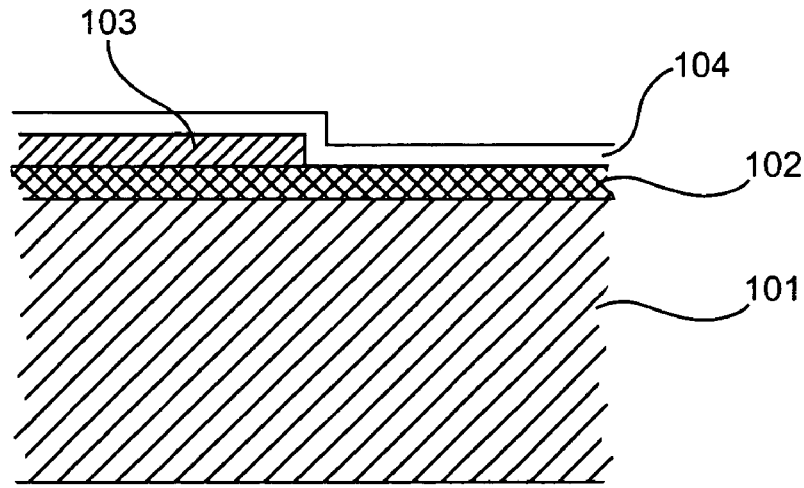

The exemplary fabrication method continues as shown in FIG. 4D by forming a spacer element 104 over the first electrode 103 and the first insulating layer 102. The spacer element 104 may be made of a variety of materials that are capable of providing insulation between the first electrode 103 and the second electrode 105. Such materials include, but are not limited to, to a polymer, photoresist, SU8 photoresist, epoxy, polyimide, Parylene®, a silicone polymer, silicon dioxide, silicon nitride, silicon oxynitride, silicon-rich silicon nitride, TEOS oxide, and plasma nitride. In certain embodiments, the second insulating layer 104 is made of silicon dioxide. The spacer element 104 may also be made up of a variety of electrically conductive materials. Such materials include, but are not limited to, metals, silicides, polycrystalline silicon, organic conductors and superconductors, electrically conductive metals and alloys of tin, copper, zinc, iron, magnesium, cobalt, nickel, platinum, and vanadium. The spacer element 104 may be removed, for example by means comprising chemical etching, in the region of nanodimensioned gap 106 and extending downward to first insulating layer 102.

The spacer element 104 may be formed atop the first electrode 103 and the first insulating layer 102 by a variety of deposition methods known in the art. For example, a deposition source, such as a vacuum evaporation source or a molecular beam epitaxy source or a sputtering source is used to deposit the spacer element 104 atop the first electrode 103 and the first insulating layer 102.

The spacer element 104 may comprise various shapes and sizes. However, it must be form a covering layer on the sidewall of first electrode 103 in the region which will later comprise nanodimensioned gap 106. In representative embodiments, the spacer element 104 covers the entire exposed surfaces of the first electrode 103 and first insulating layer 102. In representative embodiments, the spacer element 104 has a thickness ranging from about 0.5 nm to about 10 nm, including from about 1 nm to about 9 nm, such as from about 2 nm to about 8 nm, from about 3 nm to about 7 nm, from about 4 nm to about 6 nm. In certain embodiments, the spacer element 104 has a thickness of about 2 nm.

Figure 4E:
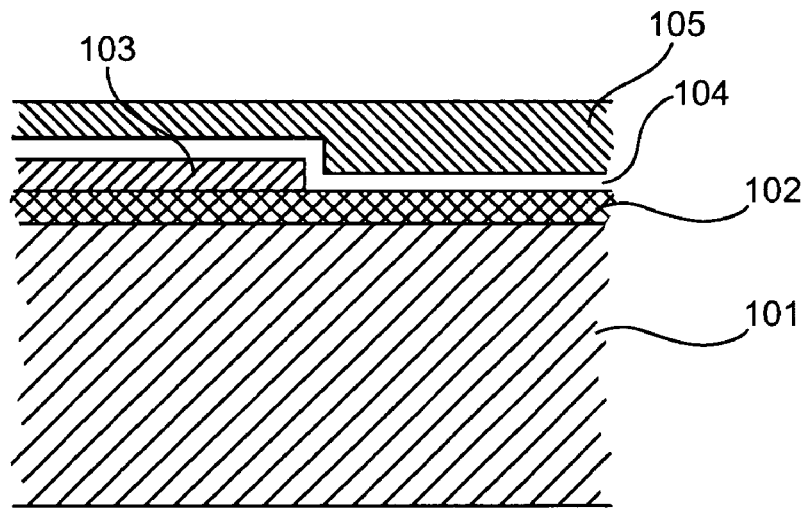

The exemplary fabrication method continues as shown in FIG. 4E by forming the second electrode 105 atop the spacer element 104. In representative embodiments, the second electrode 105 is deposited over a portion of the spacer element 104 that does not cover the first electrode 103 and the portion of the spacer element 104 that does cover the first electrode 103, as demonstrated in FIG. 5A (the region covering the first electrode 103 is represented by the dashed line). The second electrode 105 may be made up of a variety of electrically conductive materials. Such materials include, but are not limited to, metals, silicides, polycrystalline silicon, organic conductors and superconductors, electrically conductive metals and alloys of tin, copper, zinc, iron, magnesium, cobalt, nickel, platinum, and vanadium. Other materials well known in the art that provide for electrical conduction may also be employed.

In certain embodiments, the second electrode 105 is made of polycrystalline silicon. In other embodiments, the second electrode 105 is made of platinum. In some embodiments, the first electrode 103 and second electrode 105 are made of the same material. In other embodiments, the first electrode 103 and second electrode 105 are made of different materials. The second electrode 105 may comprise various shapes and sizes. However, it must be large enough and of sufficient width to cover the portion of the spacer element 104 that covers the edge of first electrode 103 in the region which will later comprise nanodimensioned gap 106, as demonstrated in FIG. 5A.

The second electrode 105 may be formed atop the spacer element 104 by a variety of deposition methods known in the art. For example, a deposition source, such as a vacuum evaporation source or a molecular beam epitaxy source or a sputtering source is used to deposit the second electrode 105 atop the spacer element 104. Next, a lithography step is performed, and etching is performed in a dilute solution of aqua regia, comprising a mixture of hydrochloric acid and nitric acid, to define the lateral extent of the second electrode 105. Alternatively, a photolithography step may be performed prior to the deposition step and second electrode 105 may be defined by means of a lift-off process.

Figure 4F:
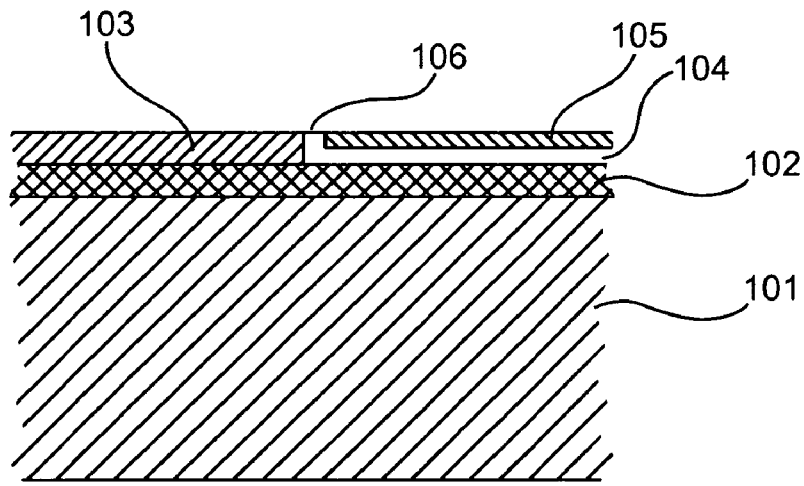
Figure 5A:
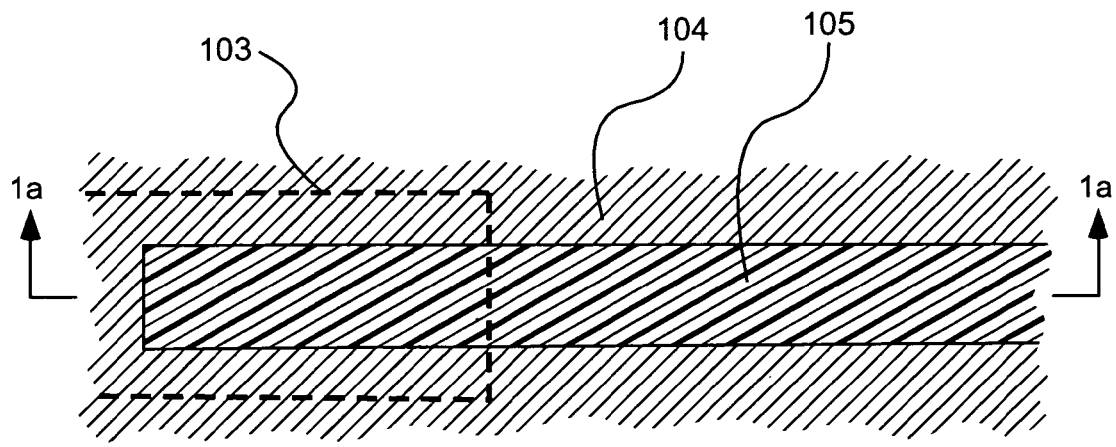
FIG. 5A is schematic illustration of a top plan view of an embodiment 100 of the present invention during a stage in the fabrication method corresponding to the stage shown in FIG. 4E. Cross-section plane 1a indicates the location of cross section shown in FIG. 4E.
Figure 5B:
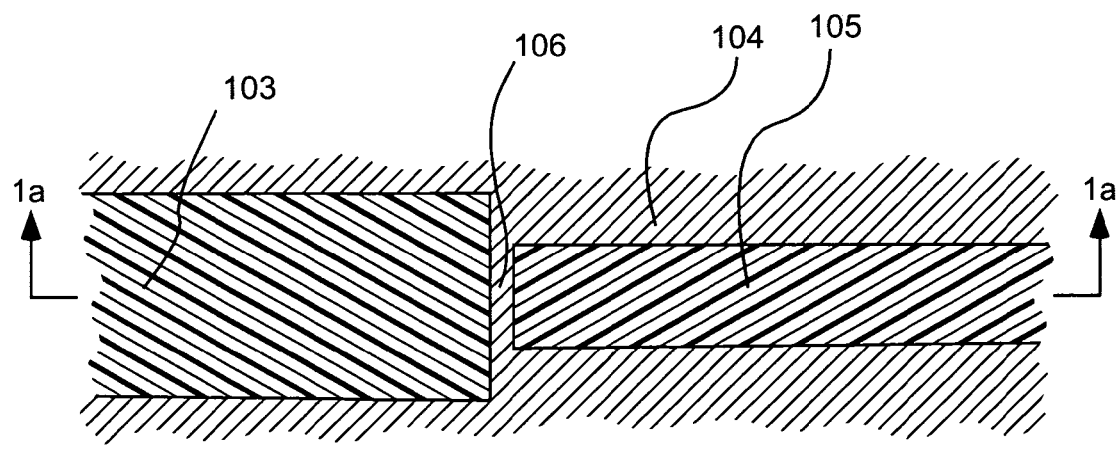
FIG. 5B is schematic illustration of a top plan view of an embodiment 100 of the present invention during a stage in the fabrication method corresponding to the stage shown in FIG. 4F. Cross-section plane 1a indicates the location of cross section shown in FIG. 4F.
Figure 6A:
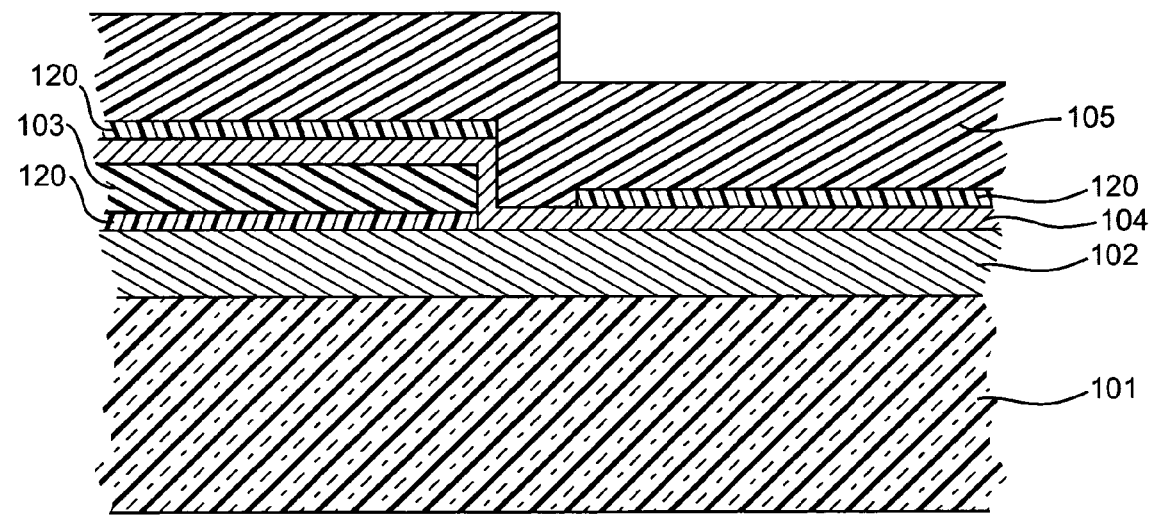
FIGS. 6A and 6B are schematic illustrations of cross-sections at plane 1a of FIG. 3 of an embodiment 100 of the present invention with the adhesion promoting layers 120.
Figure 6B:
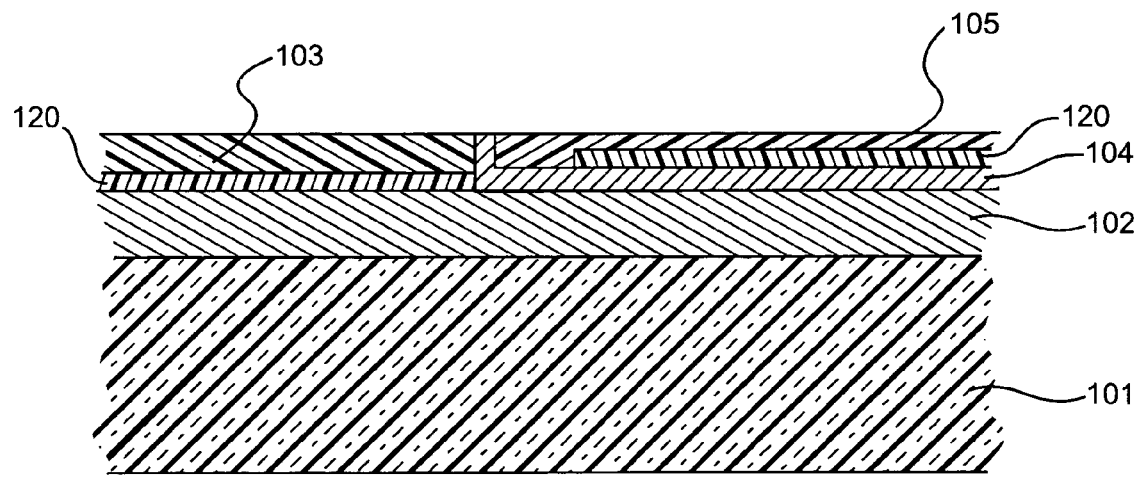
Figure 7A:
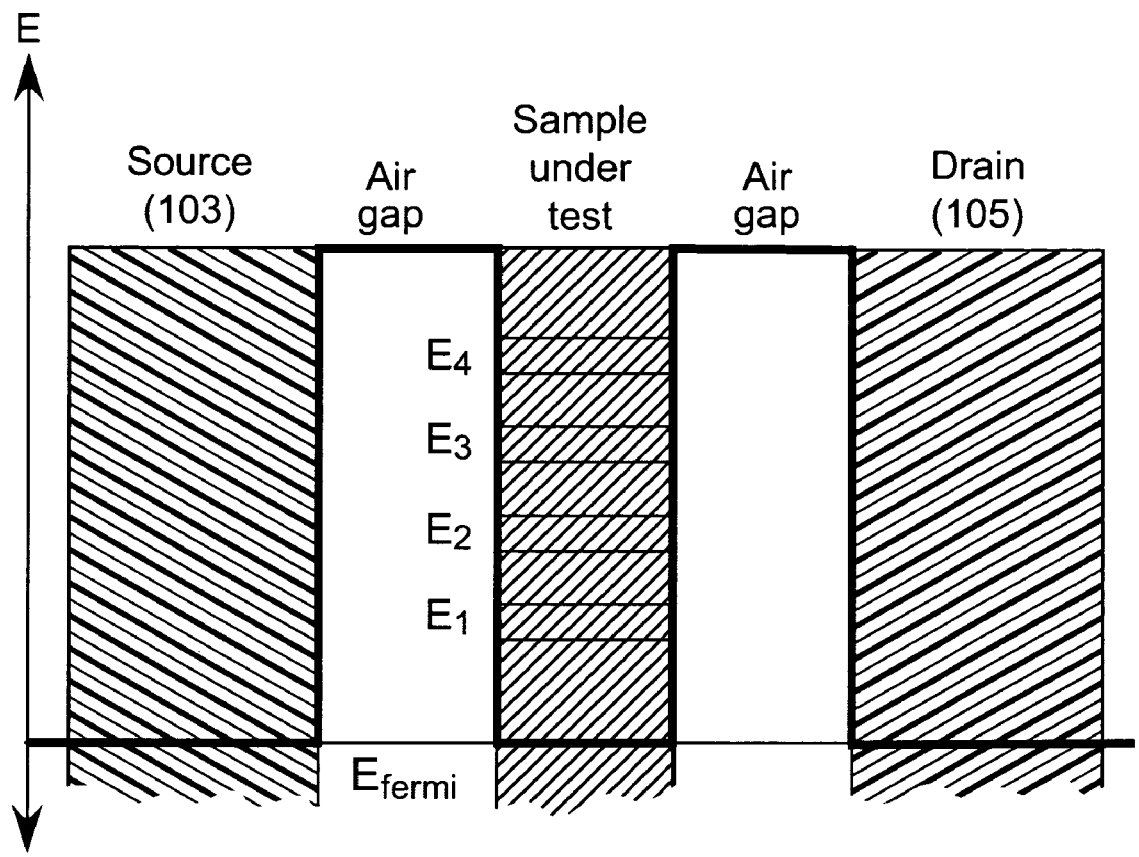
FIGS. 7A–7E are schematic illustrations of resonant tunneling conditions for a resonant tunneling spectrometer with variable geometry.
Figure 7B:
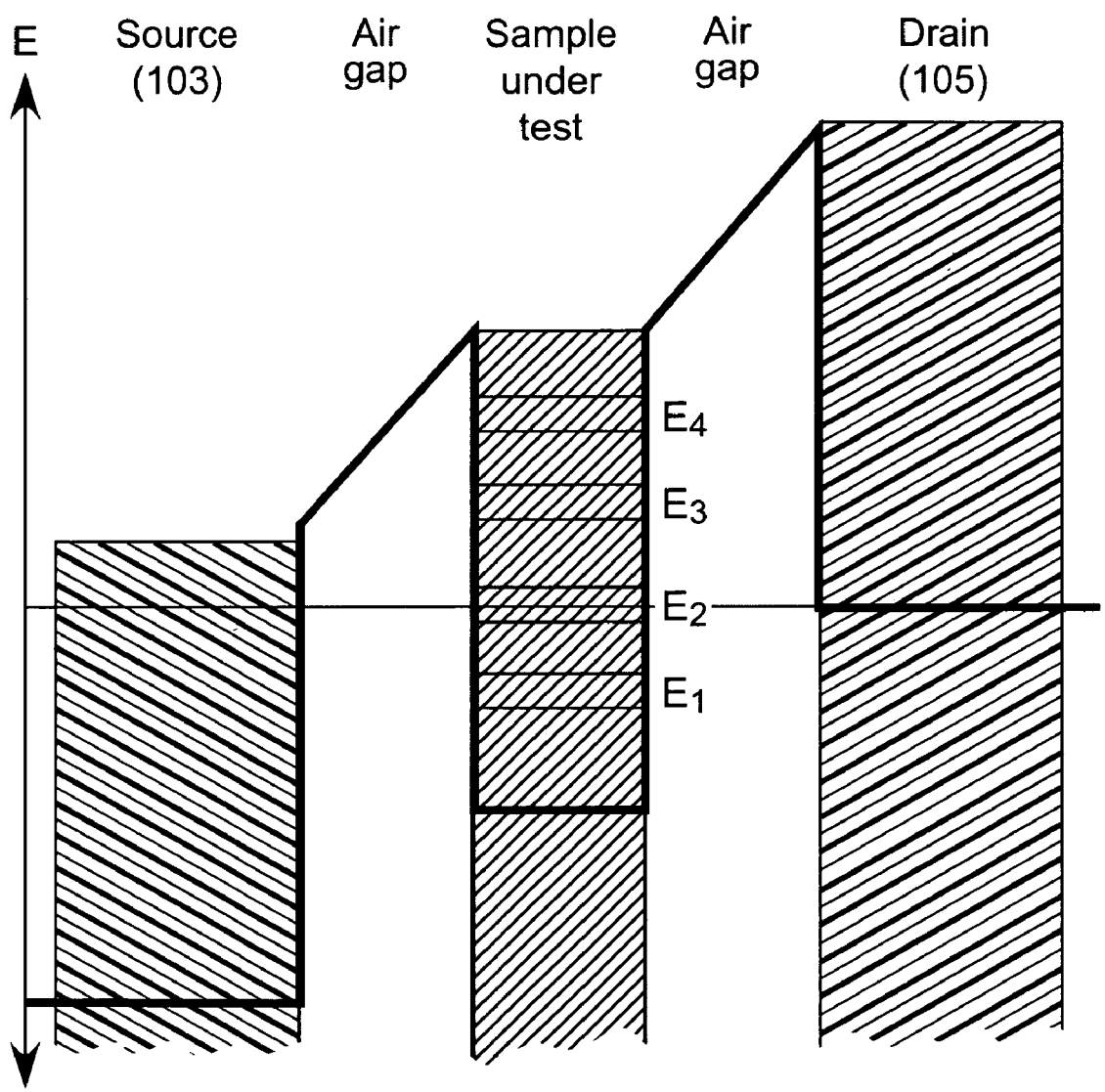
Figure 7C:
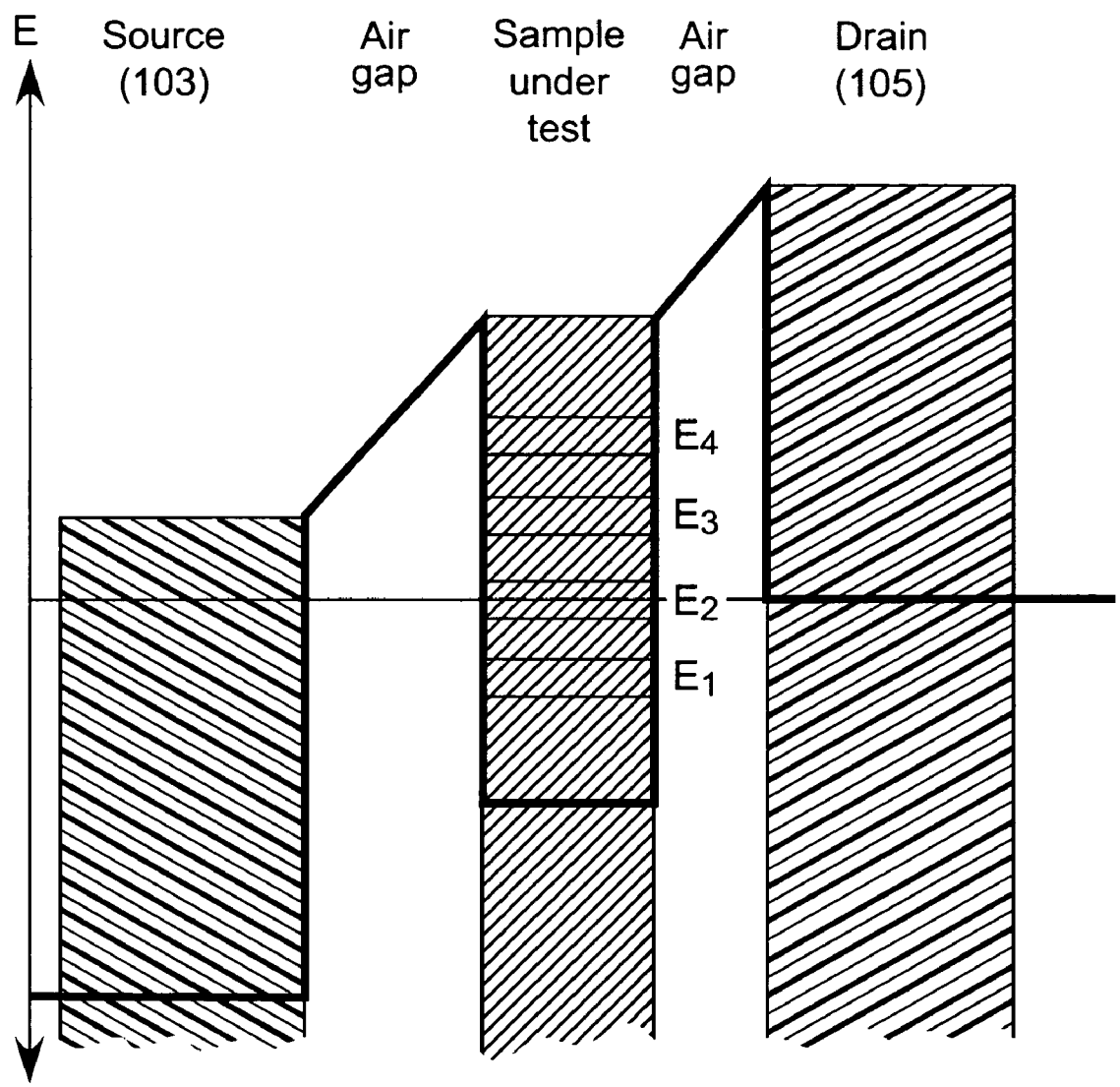
Figure 7D:
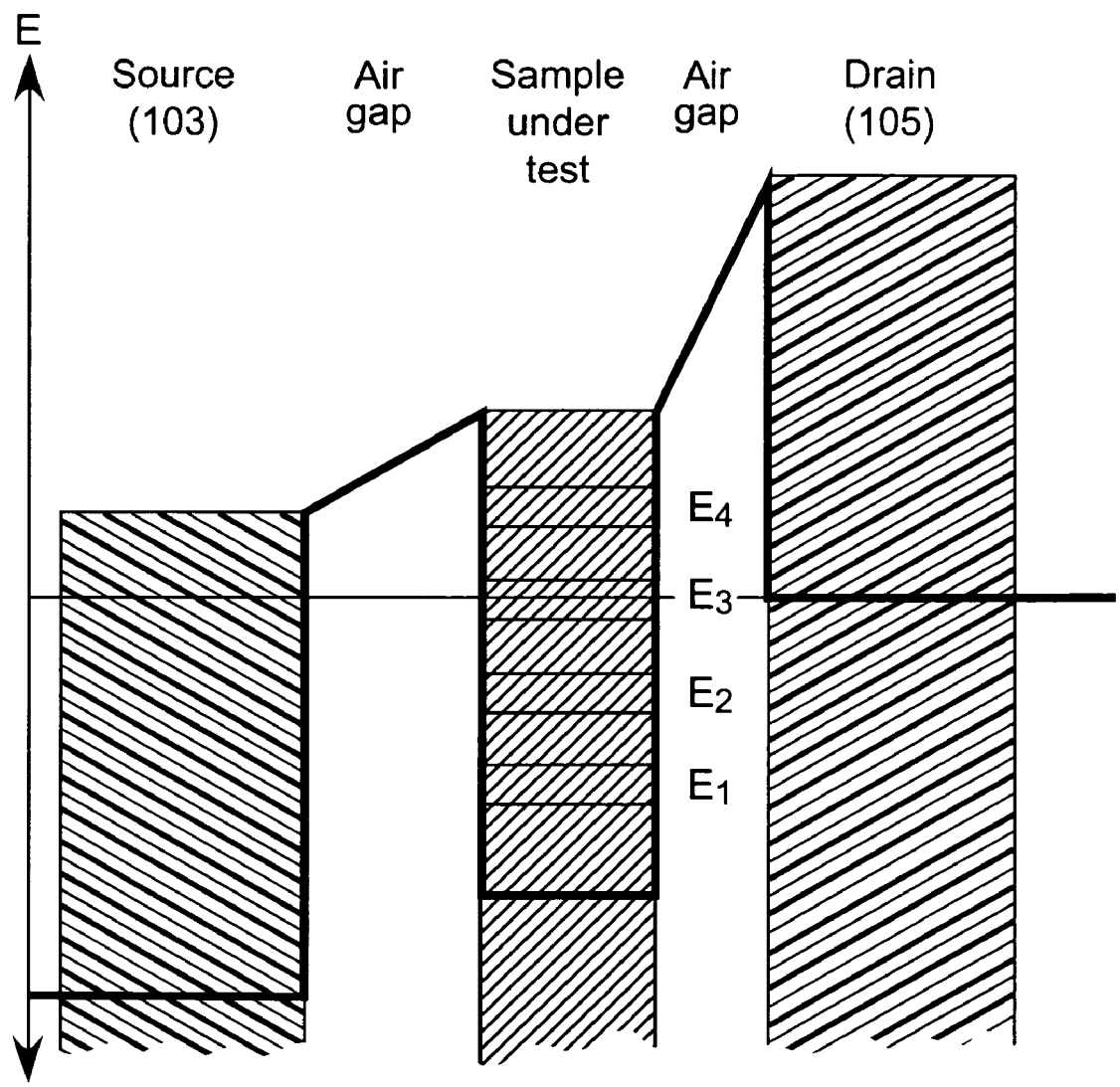
Figure 7E:
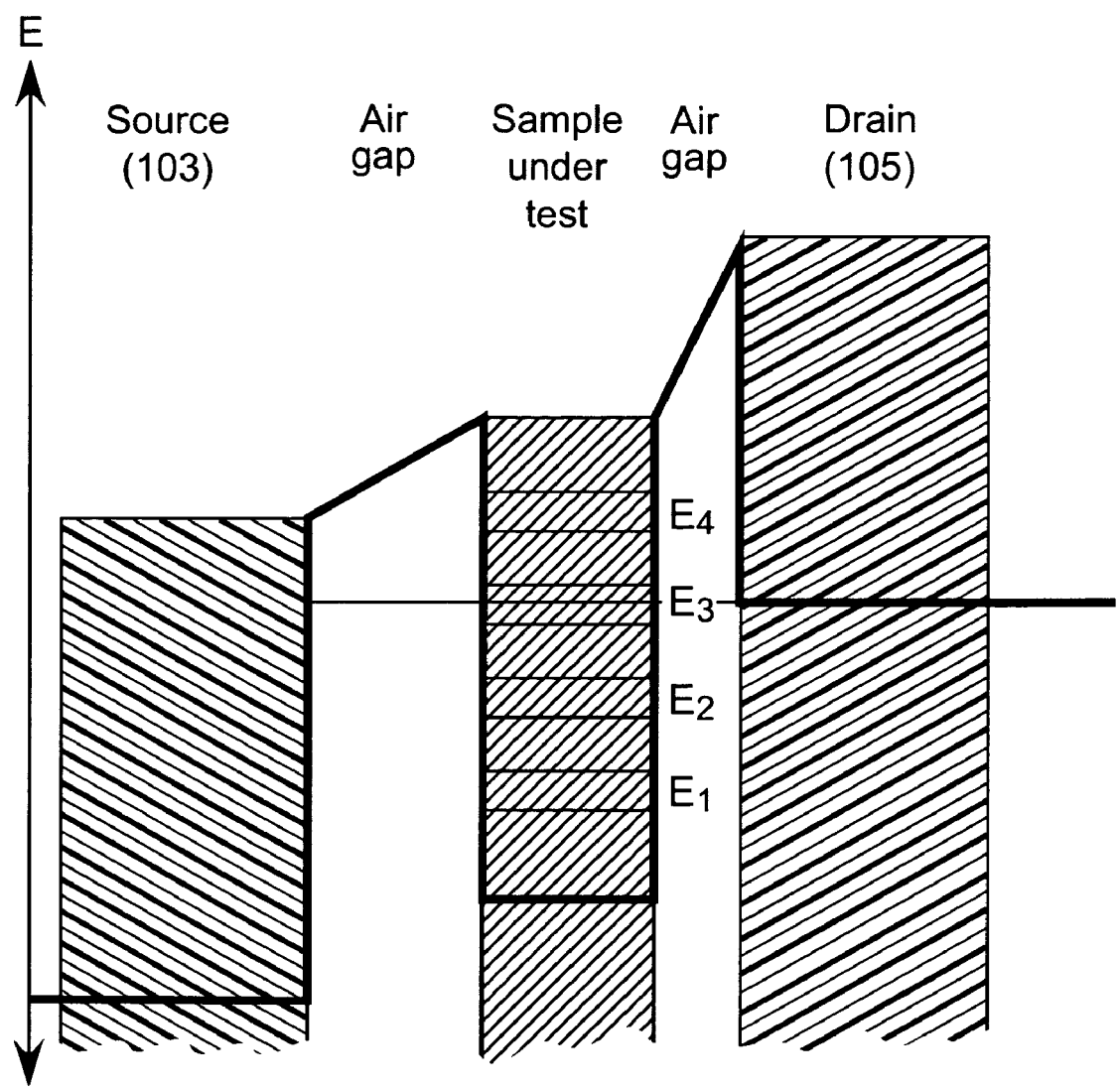

The exemplary fabrication method continues as shown in FIG. 4F by removing a portion of the second electrode 105 and a portion of the spacer element 104 in order to produce a planar surface. In representative embodiments, this step will produce a planer surface that includes a first electrode 103 and a second electrode that are separated by a nanodimensioned gap 106, wherein the nanodimensioned gap 106 is occupied by spacer element 104, as represented in FIG. 5B. The planarization of the surface of device may be performed by a variety of method well known in the art that are capable of removing a portion of the surface of an element to produce a planar surface. In some embodiments, the planarization of the surface will occur using a polishing or chemomechanical polishing (CMP) protocol. In some embodiments, the spacer element 104 is removed in the region of nanodimensioned gap 106 by means comprising a group including but not limited to chemical etching, plasma etching, and reactive ion etching. In some embodiments the removal of spacer element 104 in the region of nanodimensioned gap 106 extends down to first insulator layer 102.

The substrate 101 can then be diced by sawing to form individual chips, not shown, and electrical connection of these chips to an electrical circuit can be performed.

The final step in the preparation of the subject device is the positioning of the planar resonant tunneling sensor into device that includes a first member 107 for holding a sample and a second member 108 for moving the first member 107 and the planar resonant tunneling sensor relative to each other. The first member 107 can be made of a variety of materials that are capable of holding a sample in position above the planar resonant tunneling sensor. In some embodiments the first member 107 is an atomic force microscope (AFM) tip. In other embodiments the first member 107 is a scanning tunneling microscope (STM) tip. In representative embodiments, the first element 107 holds the sample above first electrode 103, nanodimensioned gap 106 and second electrode 105 at a distance from about 0.1 nm to about 100 nm, including form about 0.5 nm to about 10 nm, such as from about 1 nm to about 5 nm. The second member 108 can be made of a variety of materials to provide an element that is capable of moving the first member 107 and the planar resonant tunneling sensor relative to each other. In some embodiments, the first member 107 and the second member 108 are separate units that do not comprise a single integrated structure. In certain embodiments, the first member 107 and second member 108 are a single integrated structure. In representative embodiments the first member 107 and the second member 108 are an integrated structure, such as is found in an atomic force microscope (AFM), a scanning tunneling microscope (STM), and the like. In further embodiments, the first member 107 may further include an optional insulating material 117.

It will be appreciated that the fabrication sequence described above is by way of example only, and that there are other techniques well known to those skilled in the art which may be used to arrive at the same final structure. It will be appreciated also that the use of known adhesion promoter techniques between various layers will improve the yield of the fabrication process and the quality of the finished nanopore chip, and the use of such adhesion promoter techniques is assumed during the fabrication process even where not explicitly described. For example, in some embodiments, as demonstrated in FIGS. 6A and 6B, an adhesion-promoting layer 120 may be deposited atop the first insulating layer 102 and the spacer element 104 prior to the deposition of the first 103 and second 105 electrode layers. In such embodiments, the adhesion-promoting layer 120 may be made up of a variety of adhesion promoting materials, such as chromium. It will be appreciated that angled deposition techniques used to deposit adhesion-promoting layer 120 can avoid depositing material in the region of nano-dimensioned gap 106.

It will be appreciated that, while the present invention is aimed toward utility in fabrication of a device including a planar resonant tunneling sensor, it may prove to have utility for fabrication of other devices both known and unknown. Such devices include devices with microscale and nanoscale dimensions. Microscale dimensions are defined to include dimensions from 100 nm to 1 mm, and nanoscale dimensions are defined to include dimension from 0.1 nm to 1 µm.

Uses of the Subject Devices

In general, the method of using the subject device 100 of the present invention includes applying an electrical voltage between the first 103 and second 105 electrodes of the device and monitoring the electrical current between the first 103 and second 105 electrodes. The device is useful for characterizing nanocrystals, quantum dots, and macromolecules, and advantageously provides a degree of separation between sample preparation and measurement. In certain embodiments, the current flowing between the first 103 and second 105 electrode is monitored and recorded over a period of time. Therefore, the monitoring provides a range of values representing the fluctuation of the current flowing between the first 103 and second 105. In other embodiments, repeated scans of the sample are performed while different fixed voltages are applied and the current flowing between the first 103 and second 105 electrodes is measured in order to characterize the sample 116.

The sample 116 may comprise a variety of shapes, sizes and materials. The shape or size of the molecule is not important, but it must be capable of being held in position in the first member 107 for holding a sample. Exemplary samples include, but are not limited to, nanocrystals, quantum dots, macromolecules, and the like. A sample 116 is schematically depicted as a square in FIGS. 2A and 2B that is held in position in the first 107 member for holding a sample. In representative embodiments, the sample 116 resides in air or vacuum, in the absence of an aqueous solvent. In some embodiments a solvent may be present, and in some embodiments the solvent may be an aqueous solvent.

In certain embodiments, a sample 116 held in position in a first member 107 for holding a sample is scanned in the region above nanodimensional gap 106 in between the first 103 and second 105 electrodes while a time-varying electrical bias is applied between the two electrodes. As the sample 116 is moved in the space above the nanodimensioned gap and the geometry of the resonant tunneling spectrometer structures varies (i.e., the distance between the sample and the second 105 electrode decreases as the distance between the sample and first 103 electrode increases), the current is measured and recorded. As demonstrated in FIGS. 7A–7E, at specific voltages the incident energy and will match the signal representative of the internal electronic band structure of the sample.

In another embodiment, the device 100 includes a triode structure comprising a resonant tunneling sensor, wherein the first member 107 for holding a sample is made of a conductive material, such as a STM tip. In such embodiments, a tunneling current due to the phenomenon of resonant tunneling occurs from one electrode, to the sample under test, and thence to another electrode. The magnitude and phase of the tunneling current depend on the spatial position and orientation of the sample under test, on the internal electronic band structure of the sample under test, and on the voltages applied to the three electrodes in the triode structure. The resulting resonant tunneling spectrum provides information on the makeup of the sample under test. Advantageously, the applied voltage needed to obtain spectral data may be minimized. In some embodiments, the STM tip may be coated with an insulator which sits between the conductive portion of the STM tip and the sample under test.

The matched-barrier resonance provides nanometer-scale spatial resolution within the volume of the sample under test. Additionally, the matched-barrier resonance provides an enhancement of the resonant tunneling current, which is used as a signal representative of the internal electronic band structure of the sample under test. In further embodiments, the device may also be employed in a dielectrometry mode, such as a dielectrometry sensor, further described in U.S. Pat. No. 6,380,747 and U.S. Patent Application No. 20020075006, the disclosures of which are incorporated herein in their entirety.

It will be appreciated that the utility of the structures and processes described herein has been discussed with respect to the theory of resonant tunneling, but that the utility of these structures and processes is in no way limited to resonant tunneling, but instead applies also to other physical phenomena useful for measurement and manipulation of small object including biopolymers, including but not limited to non-resonant tunneling, electrostatic attraction and repulsion, fluidic field effect transistors, electrolysis, and the like. Either one or both of the electrodes 103 and 105, or the insulator element 104 between electrodes 103 and 105, might be coated with a monolayer of a molecule useful for binding to or detecting a biopolymer molecule of interest.

In certain embodiments, the subject methods also include a step of transmitting data or results from the monitoring step, as described above, to a remote location. By "remote location" is meant a location other than the location at which the translocation occurs. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A sensor device comprising:
   a first electrode presenting a planar surface at a planar surface of a substrate;
   a second electrode presenting a planar surface at said planar surface of said substrate and spaced apart by a gap from said first electrode, wherein said gap has a width ranging in length from about 1 nm to about 8 nm;
   a first member capable of holding a sample under test; and
   a second member attached to said first member and capable of moving said sample under test over said gap in relative direction from said first electrode to said second electrode.

2. The device according to claim 1, wherein said first member comprises atomic force microscopy (AFM) tip.

3. The device according to claim 1, wherein said first member is positioned above said surface at a distance ranging from about 0.1 nm to about 100 nm.

4. The device according to claim 1, wherein said nanodimensioned gap is occupied by a spacer element comprising an insulating material.

5. The device according to claim 4, wherein said insulating material comprises silicon dioxide.

6. The device according to claim 1, wherein said first and second electrodes comprise platinum.

7. The device according to claim 1, wherein said first and second electrodes comprise polycrystalline silicon.

8. The device according to claim 1, wherein said planar substrate comprises single-crystal silicon.

9. A method for fabricating the device according to claim 1, said method comprising:
 (a) providing a first insulator layer atop a planar substrate;
 (b) depositing a first conductive layer on a first portion of said first insulator layer;
 (c) depositing a spacer element layer over said first conductive layer and a second portion of said surface of said first insulator layer;
 (d) depositing a second conductive layer over a portion of spacer element layer; and
 (e) removing a portion of said second conductive layer and said spacer element layer to produce a structure comprising first and second electrodes present on a surface of a planar substrate and separated from each other by a nanodimensioned gap to produce the device according to claim 1.

10. The method according to claim 9, wherein said removing step (d) comprises polishing said surface to produce a flat surface.

11. The method according to claim 10, wherein said polishing comprises using a chemomechanical polishing protocol.

12. The method according to claim 9, wherein said method further comprises positioning said sensor in a device that further includes:
 a first member for holding a sample; and
 a second member for moving said first member and planar resonant tunneling sensor relative to each other.

13. A method comprising:
 (a) positioning a sample on a first member of the device according to claim 1; and
 (b) moving said positioned sample relative to said first and second electrodes.

14. The method according to claim 13, wherein said method comprises maintaining a constant first voltage applied to said first and second electrodes while sample is moved relative to said electrodes.

15. The method according to claim 14, wherein said method further comprises reiterating step (b) at least once at a second voltage that is different from said first voltage.

16. The method according to claim 13, wherein said method is a method for characterizing a quantum dot.

17. The method according to claim 13, wherein said method is a method of characterizing a macromolecule.

18. The method according to claim 13, wherein said method of characterizing is a method of characterizing a nanocrystal.

\* \* \* \* \*